US009144384B2

(12) United States Patent
Margarida et al.

(10) Patent No.: US 9,144,384 B2
(45) Date of Patent: Sep. 29, 2015

(54) METHOD, SYSTEM AND APPARATUS FOR CONTINUOUS CARDIAC MONITORING OF AN INDIVIDUAL

(75) Inventors: Cesar Claudio Margarida, Sao Paulo (BR); Marcelo de Campos Roriz, Jr., Sao Paulo (BR); Antonio Andre Neto, Sao Paulo (BR)

(73) Assignee: CORCAM TECNOLOGIA S.A., Sao Paulo-SP (BR)

( * ) Notice: Subject to any disclaimer, the term of this patent is extended or adjusted under 35 U.S.C. 154(b) by 21 days.

(21) Appl. No.: 13/536,614

(22) Filed: Jun. 28, 2012

(65) Prior Publication Data
US 2013/0237861 A1 Sep. 12, 2013

(30) Foreign Application Priority Data

Mar. 6, 2012 (BR) ........................ 10 2012 005038 2

(51) Int. Cl.
*A61B 5/0205* (2006.01)
*A61B 5/02* (2006.01)
(Continued)

(52) U.S. Cl.
CPC ................ *A61B 5/02* (2013.01); *A61B 5/0006* (2013.01); *A61B 5/0022* (2013.01); *A61B 5/0205* (2013.01); *A61B 5/0402* (2013.01); *A61B 5/11* (2013.01); *A61B 5/7264* (2013.01); *A61B 5/747* (2013.01); *A61B 5/0404* (2013.01); *A61B 5/0452* (2013.01); *A61B 5/1112* (2013.01); *A61B 5/1117* (2013.01); *A61B 5/743* (2013.01)

(58) Field of Classification Search
CPC .. A61B 5/0006; A61B 5/0022; A61B 5/1117; A61B 5/7267; A61B 5/0402; A61B 5/002; A61B 5/0205; A61B 5/1113; A61B 5/1112; A61B 5/7275; A61B 2560/045; A61B 5/024; A61B 5/7264; A61B 5/02; A61B 5/02438; A61B 5/747; G06F 19/3418; G06F 19/345; G06F 19/321; G06F 19/322; G06F 19/3406; G06F 19/3443; G06F 19/3487; G06Q 50/22; G08B 21/02; G08B 21/0446; G08B 21/0453
USPC .............. 600/508–509, 513, 515, 527; 607/9, 607/17–19, 32, 60, 62; 128/903, 920, 128/923–925
See application file for complete search history.

(56) References Cited

U.S. PATENT DOCUMENTS 4,827,943 A 5/1989 Bornn et al.
5,967,981 A 10/1999 Watrous
(Continued)

FOREIGN PATENT DOCUMENTS

BR PI0603602 4/2008
BR PI0800287 9/2009
(Continued)

OTHER PUBLICATIONS

PCT International Search Report; PCT/BR2012/000360; Feb. 6, 2013; 4 pages.

*Primary Examiner* — Deborah Malamud
(74) *Attorney, Agent, or Firm* — Hamre, Schumann, Mueller & Larson, P.C.

(57) ABSTRACT

A method, a system and an apparatus for remotely monitoring a cardiac condition in an individual in which there is provided a non-invasive, mobile and portable solution including hardware, software, and a back-office application allowing an autonomous and smart remote monitoring. Two-way communication is provided between the cardiac monitoring apparatus and a monitoring center, which allows sending of data of the patient being monitored to the monitoring center, as well as allowing the monitoring center or a clinician to request a new exam on demand.

17 Claims, 7 Drawing Sheets

(51) Int. Cl.
*A61B 5/0402* (2006.01)
*A61B 5/11* (2006.01)
*A61B 5/00* (2006.01)
A61B 5/0404 (2006.01)
A61B 5/0452 (2006.01)

(56) References Cited

U.S. PATENT DOCUMENTS

| | | | |
|---|---|---|---|
| 6,287,252 | B1 | 9/2001 | Lugo |
| 6,402,691 | B1 | 6/2002 | Peddicord et al. |
| 7,289,844 | B2 | 10/2007 | Misczynski et al. |
| 7,558,622 | B2 * | 7/2009 | Tran ................................ 600/509 |
| 2006/0052717 | A1 | 3/2006 | Mugler et al. |
| 2011/0004110 | A1 * | 1/2011 | Shusterman ................. 600/509 |

FOREIGN PATENT DOCUMENTS

| | | |
|---|---|---|
| BR | PI0804086 | 7/2010 |
| CN | 101579235 | 7/2011 |
| CN | 201898620 | 7/2011 |
| KR | 20060117546 | 1/2008 |
| WO | 03075118 | 9/2003 |
| WO | 03082093 | 12/2003 |
| WO | 2009142975 | 11/2009 |
| WO | 2011133799 | 10/2011 |

* cited by examiner

Fig. 4

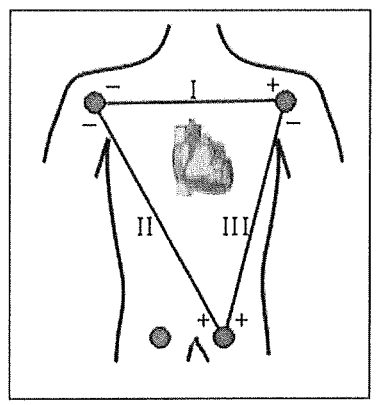
FIG. 6
FIG. 7
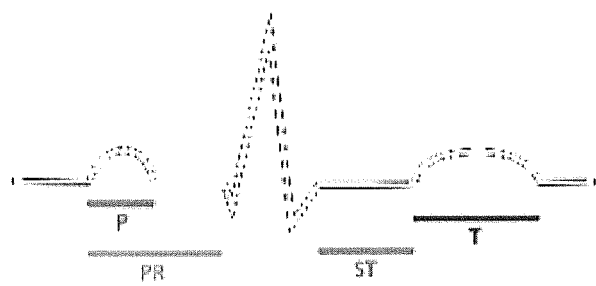

METHOD, SYSTEM AND APPARATUS FOR CONTINUOUS CARDIAC MONITORING OF AN INDIVIDUAL

FIELD

The present disclosure relates to a method, a system and an apparatus for remotely monitoring a cardiac condition in an individual in which there is provided a non-invasive, mobile and portable solution including hardware, software, and a back-office application allowing an autonomous and smart remote monitoring.

BACKGROUND

Cardiovascular diseases are the main cause of death worldwide, arising primarily from the lifestyle and food intake of individuals, as well as from congenital predispositions. Smoking, high cholesterol levels, high blood pressure, engaging in a sedentary lifestyle, and diabetes are factors influencing the occurrence of heart diseases. According to data from the World Health Organization (WHO), heart diseases account for 12% of all deaths.

Heart diseases have worldwide assumed an epidemic status, and despite the advancements in the development of pharmaceuticals, surgical techniques and medical practices, there is still a need for providing new and improved means for preventing cardiac conditions of an individual.

For example, the cardiac condition monitoring of individuals, thus far the best way of prevention, can be performed by regularly visiting the cardiologist, in which electrocardiogram (ECG) comprises the primary means for detecting changes in the cardiac condition of an individual.

The remote monitoring known in the art comprises the use of equipment attached to the individual, in which the current ECG monitoring equipment typically remains beside the patient, not allowing for free movement or rendering the remote monitoring difficult. The current options of wireless cardiac monitoring devices generally employ: RF (radio frequency) transmitters and receptors, or communication via Bluetooth (protocol 802.15.1), restricting to a few units the number of equipment simultaneously monitored as well as the distance, which is limited to about 10-20 meters. All currently available options only send data from the patient user to the clinician, thus leaving no possibility of on-demand request; i.e., bilateral.

SUMMARY

A method, system, and apparatus for remotely monitoring the cardiac condition of an individual are described.

The apparatus for remotely monitoring the cardiac condition of an individual is portable, mobile, and non-invasive, including hardware, software and a back-office application which allows for smart and autonomous remote monitoring via Global System for Mobile Communications/General packet radio service (GSM/GPRS), detecting cardiac intercurrences (arrhythmias and ischaemias) through 3 electrodes (derivations I, II and III), patient falls, as well as integrating hands-free assistance and geographical localization via Global Positioning System (GPS).

In one method for remotely monitoring a cardiac condition of an individual, there is provided a two-way interactivity between the patient and a monitoring center, since in addition to sending data of the patient being monitored to the monitoring center (MC), at any given moment, the MC or a clinician may conditionally request a new exam on demand, thus allowing an actual and accurate tracking without the need of displacing the patient being monitored.

The known prior art discloses remote monitoring of a cardiac condition of an individual by reading an ECG, having local storage of data collected, and sending the data to a remote station or database file of ECG records, in addition to sending a wanting and the location of the individual via GPS and Enhanced Data rates for GSM Evolution (EDGE) technologies. However, prior art systems are not directed to the monitoring and identification of ischaemias, and do not offer hands-free communication which provides such an interactivity that it becomes possible to make bilateral or two-way requests regardless of the condition of the individual being monitored. Furthermore, known systems do not have a neural network that allows establishing a customized cardiac profile of the individual, do not provide means for detecting falls nor providing a voice command, which function to significantly improve the monitoring form and the response in critical scenarios.

DRAWINGS

Figure 4:
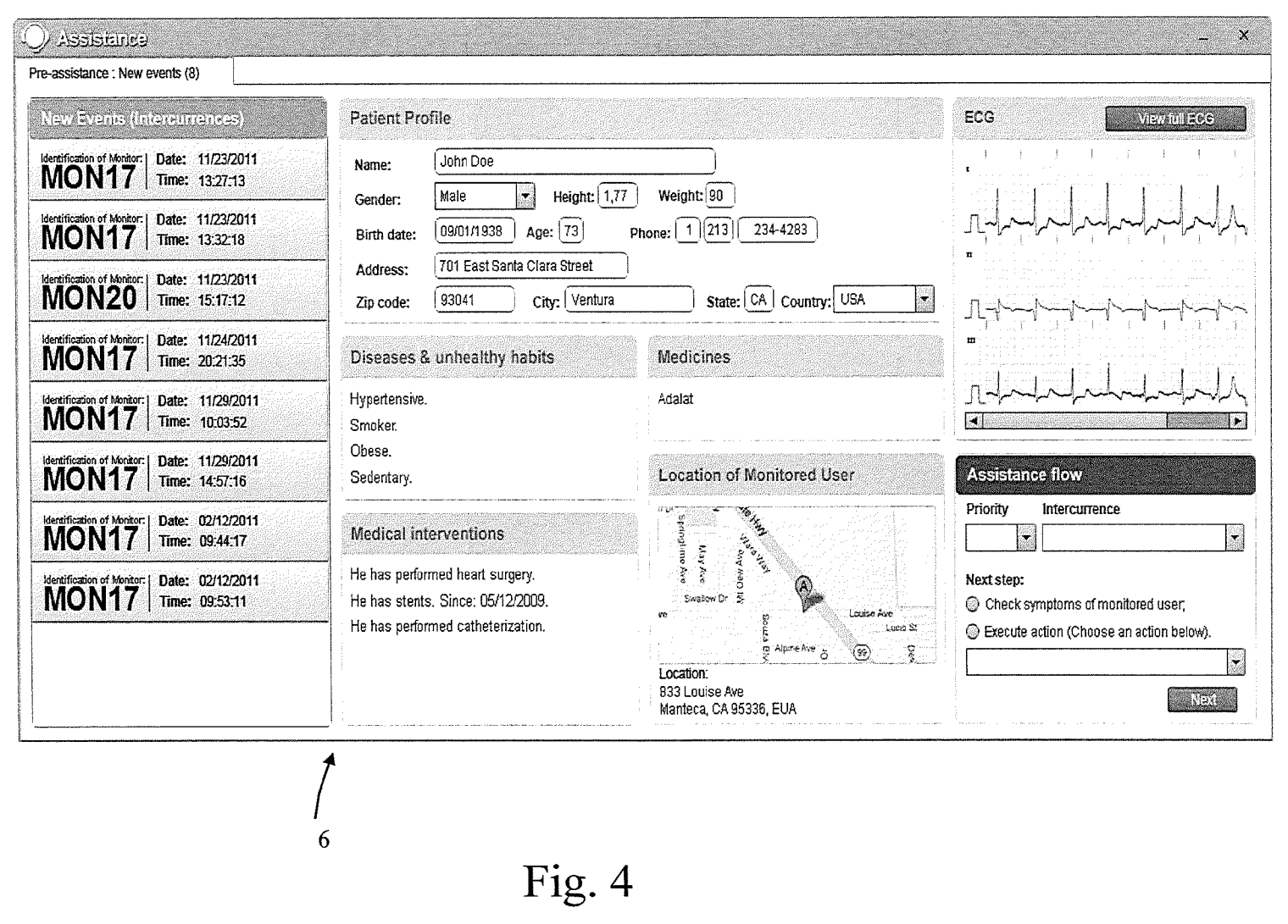

FIG. 4 schematically shows a user interface screen of the data interface described herein.

Figure 5:
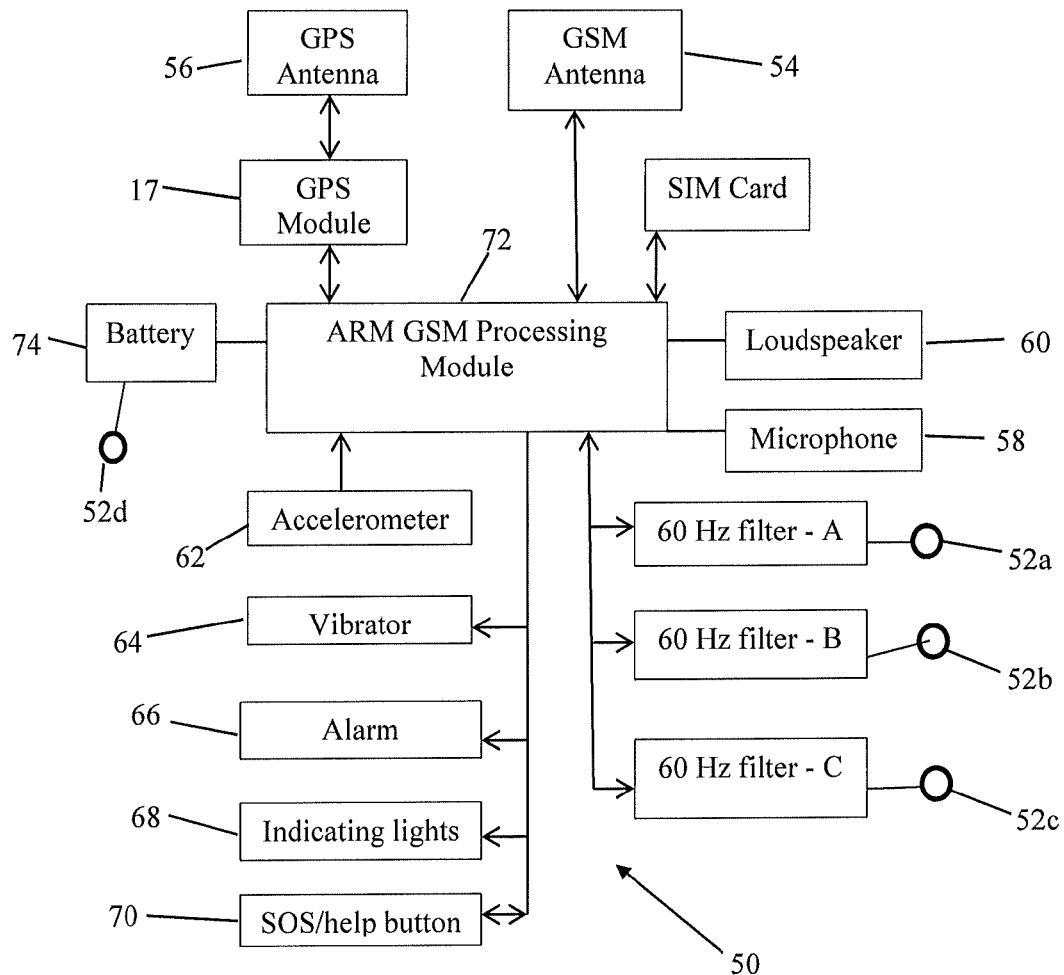

FIG. 5 is a schematic diagram of the patient monitoring apparatus described herein.

FIG. 6 illustrates an exemplary arrangement of the electrodes on a patient to obtain an ECG.

FIG. 7 shows an exemplary wave pattern graph in a period of one ECG.

Figure 8:
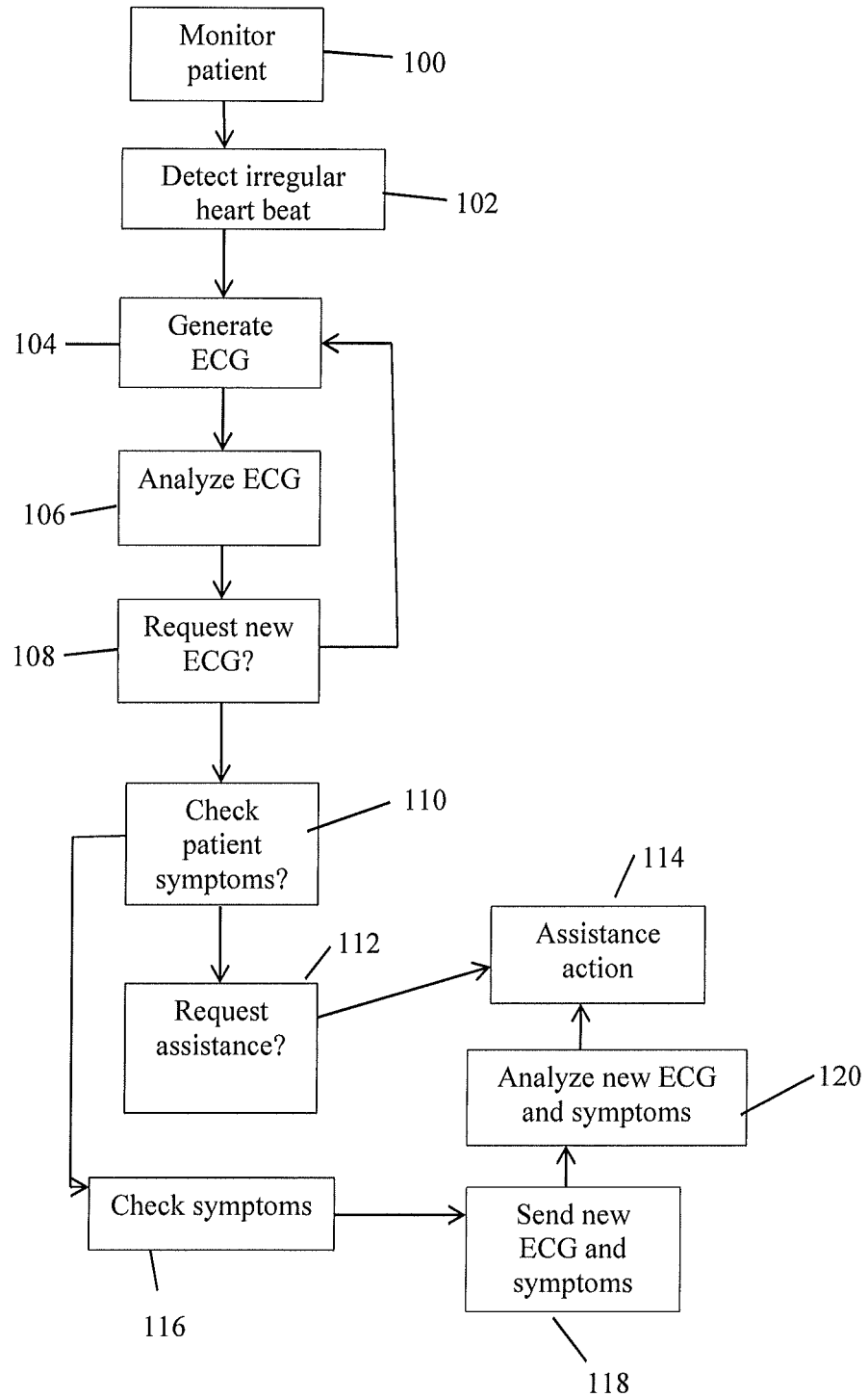

FIG. 8 is a flow diagram of the assistance routine of the cardiac monitoring described herein.

DETAILED DESCRIPTION

This description describes a method for monitoring the cardiac condition of a patient in which there is provided a monitoring network which enables the continuous monitoring of the cardiac condition of the patient allowing the patient and the clinician to remotely interact and providing the clinician with a tool for collecting, monitoring and viewing electrocardiograms in real time and over the Internet.

In this way, the patient will be able to have his/her cardiac condition analyzed by a clinician or medical staff at any time, wherever the patient is located.

Figure 1:
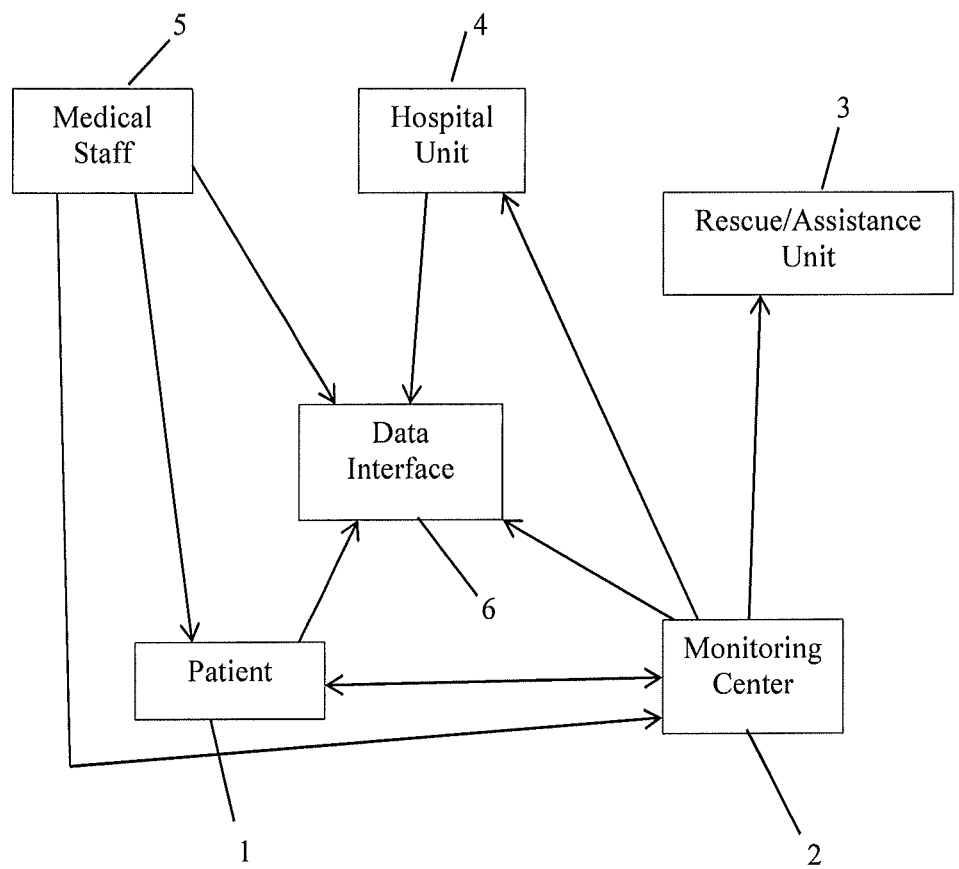
FIG. 1 is a schematic diagram of a method and system described herein.

With reference to FIG. 1, the method includes establishing a remote, 2-way communication between an individual 1 whose cardiac condition is being monitored and a Monitoring Center (MC) 2. The method can also include establishing a remote communication between the MC 2 and a Rescue/Assistance Unit 3; establishing a remote communication between the MC 2 and a Hospital Unit 4; establishing a remote communication between the individual 1 whose cardiac condition is being monitored and Medical Staff 5; and establishing a Data Interface 6 that is remotely accessible to registered users, for example via a website on the internet.

The remote communication, for example, between the individual 1 and the MC 2 is established in a two-way fashion, i.e. both the individual 1 and the MC 2 are able to mutually make requests of one another such that the assistance and the updating of data and information in real time are streamlined.

The communication between the individual 1 and the MC 2 can be achieved by any suitable communication means, for example by means of GSM and GPS communication. This enables an interaction between the individual 1 and the MC 2 allowing requests to be readily forwarded as well as the individual 1 to be quickly positioned in an emergency situation for ready assistance.

ECG readings of the individual 1 will be continuously carried out by means of software embodied into a remote monitoring apparatus accompanying the user (shown in FIG. 5), the detailed description of which will be provided hereinafter. In a critical situation, a reading which identifies an irregularity in the cardiac condition of the individual will be sent to the MC 2 as an ECG exam together with further parameters which will be later defined below.

The ECG warning sent from the apparatus monitoring the individual 1 will trigger in the MC2 a user assistance provision protocol which can include a closest Rescue/Assistance Unit 3 and the Hospital Unit 4 to be mobilized for ready assistance. The user assistance provision protocol can comprise a monitored profile of the individual 1 and the individual's location for rescue actions. Detailed information about the individual 1 profile can also be accessed on the Interface 6 which can be updated in real time which will allow both the Rescue/Assistance Unit 3 and the Hospital Unit 4 to speed up the medical assistance regarding the cardiac condition of the individual 1.

The Interface 6 can be accessed upon registration on a suitable website and allows access to profile information of the individual 1 in emergency situations, but also for routine control. For example, an individual 1 may have his/her records accessed by medical staff in charge of following up with that patient regularly, thus being possible to remotely follow up concerning an administered treatment, a post-operative period, or even the reaction of the individual to a new prescribed drug.

It is to be understood that the term "communication" used herein includes, but is not limited to, the sending and reception of formal communications (for example via telephone networks), text and/or voice messages and data transfer via GSM communication. In the illustrated embodiment, only the communication between the individual 1 and the MC 2 is carried out in a two-way fashion; that is, the individual 1 and the MC 2 can reciprocally receive requests via suitable communication means such as GSM.

A system for remotely monitoring the cardiac condition of an individual is also described. In the illustrated example in FIG. 3, the system comprises two module branches including a main branch 10 that carries out the cardiac condition monitoring routines on the individual 1 and a managing branch 12 that carries out the routines interconnecting the network in the described method.

Figure 2:
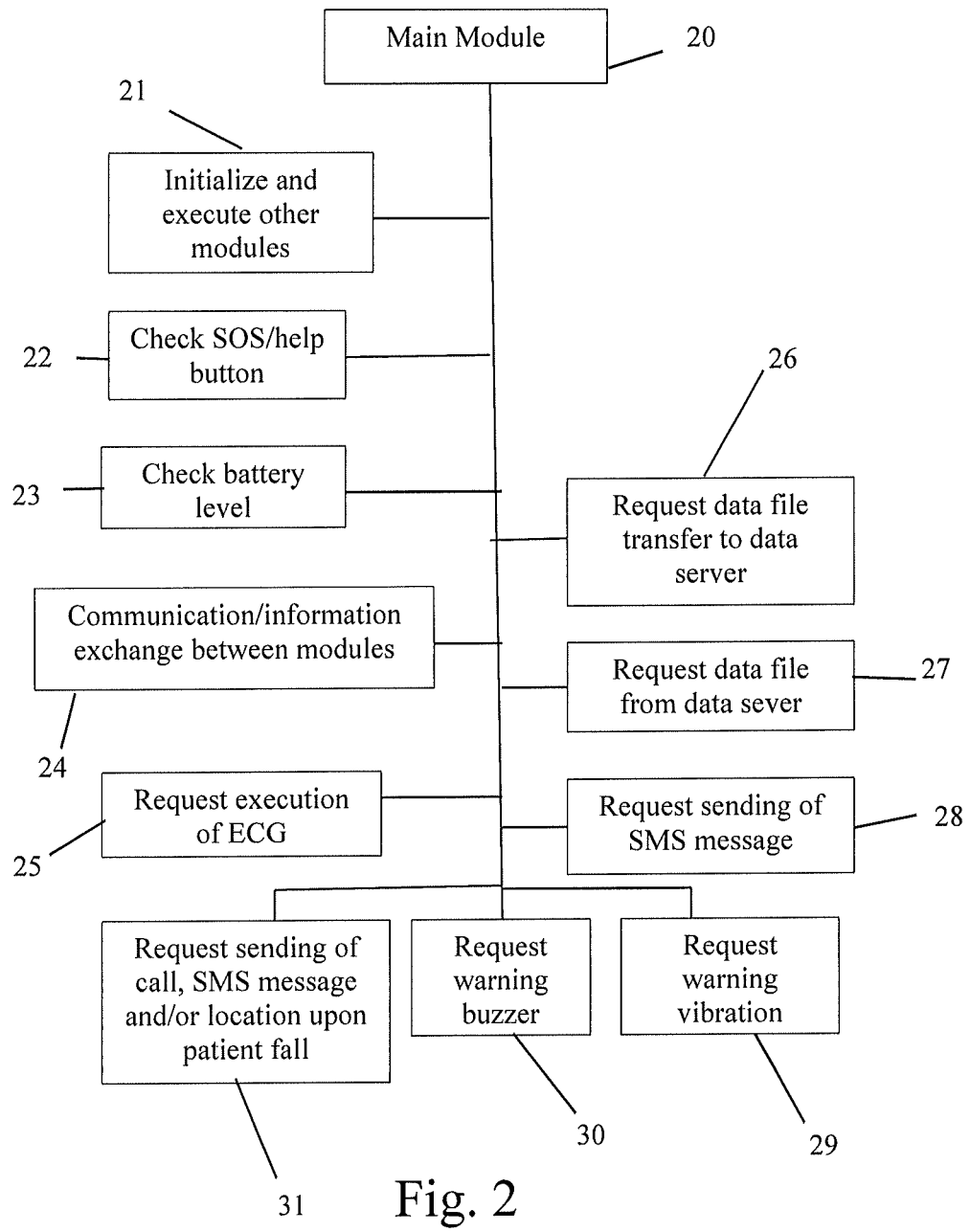
FIG. 2 is a diagram showing the routines carried out by the main module of the main branch of the disclosed system.
Figure 3:
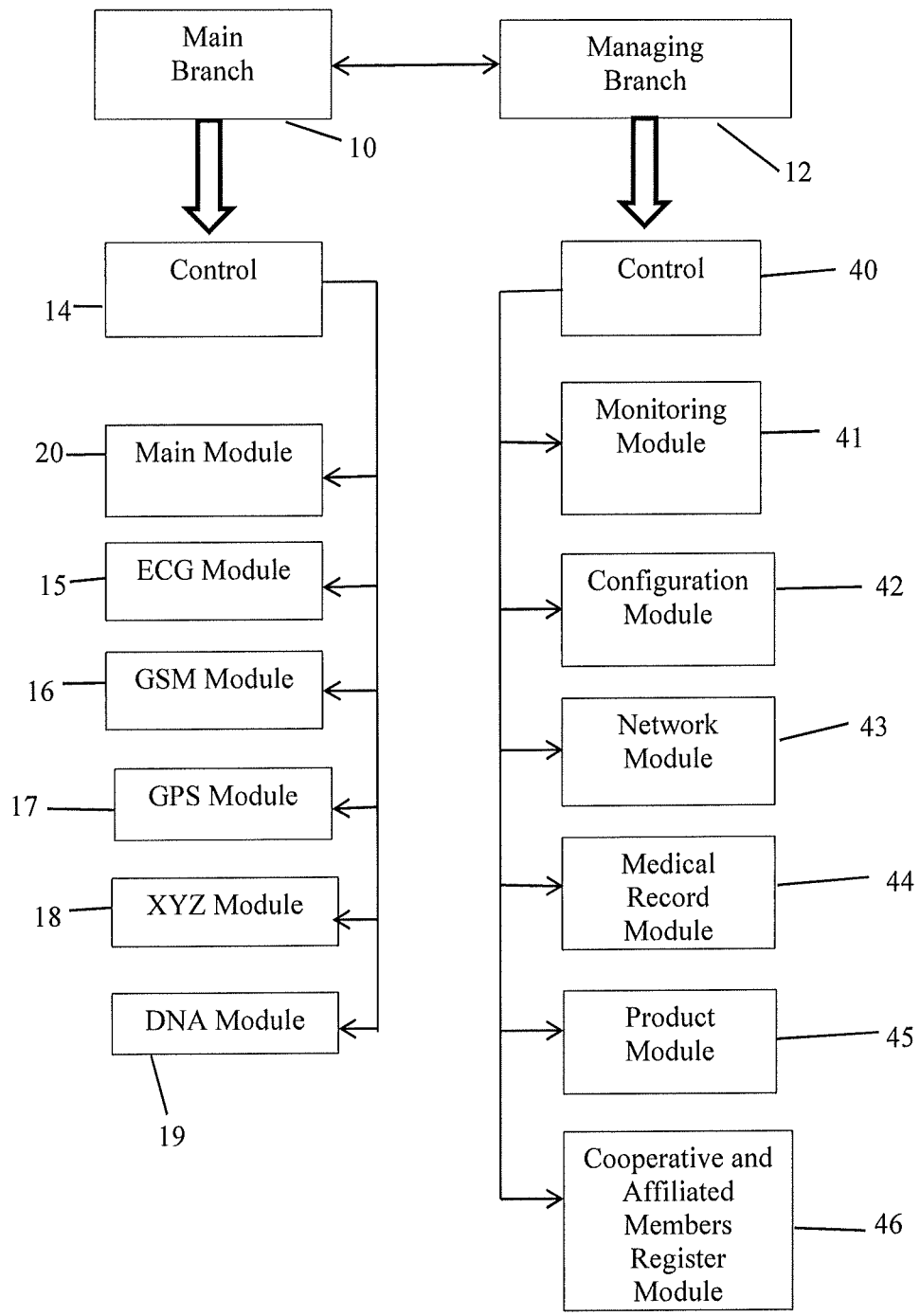
FIG. 3 is a diagram showing the modules of the main branch and the managing branch of the disclosed system.

With reference to FIG. 3, the main branch 10 includes the following routine modules under the control of a controller 14:

A Main Module 20—The Main Module 20 is configured to perform the activation functions of the patient monitoring apparatus of FIG. 5 by carrying out the following routines shown in FIG. 2:

Initializing the environment and executing other modules 21;
Checking the SOS/help button 22;
Checking the Battery level 23;
Handling communication and information exchange between all the modules 24;
Requesting the execution of the ECG 25;
Requesting the transfer of data file(s) to a data server 26;
Requesting the downloading of data file(s) from the data server 27;
Requesting the sending of Short Message Service (SMS) text message(s) 28;
Requesting the monitoring apparatus to vibrate as a warning means 29;
Requesting the buzzer of the monitoring apparatus to emit sound as a warning means 30;
Requesting an emergency call and/or sending SMS and/or location warning upon detecting a user fall 31 via the accelerometer of the monitoring apparatus.

An ECG Module 15—the ECG module 15 is configured so as to be responsible for generating ECG exams and checking cardiac intercurrences such as ischaemias or arrhythmias.

A GSM Module 16—the GSM module 16 is configured so as to be responsible for operating the communication via GSM/GPRS (Global System for Mobile Communications/General Packet Radio Service) and outputting sound through the buzzer. This module 16 can also control communications via hands-free phone calls and by sending and receiving SMSs. The module 16 can also be responsible for transferring data files and data from the monitoring apparatus to the data server and vice versa. Any SMSs received in encoded form, after being identified to the requested operations, are forwarded to the main module 20 which will take proper measures.

A GPS Module 17—the GPS module 17 is configured so as to be responsible for reading GPS (Global Positioning System) data from the monitoring apparatus and reading the retrieved latitude and longitude coordinates. Those coordinates are forwarded to the main module 20, which in turn forwards this information to the ECG module 15.

An XYZ Module 18—the XYZ module 18 is configured so as to be responsible for reading and evaluating the coordinates of the accelerometer of the monitoring apparatus. This module 18 detects when the monitoring apparatus moves or falls (i.e. when the individual 1 falls). By detecting a fall, the XYZ module 18 notifies the main module 20 to take the proper measures.

A DNA Module 19—the DNA module 19 is configured so as to be responsible for the Probabilistic Neural Network (PNN) for detecting intercurrences (arrhythmias and ischaemias). PNN's are known. The most important property of neural networks lies in their ability to learn from the environment, thus improving their performance. This happens through a dynamic adjustment process applied to their weights on the training. The learning occurs when the neural network achieves a generalized solution for a class of problems. As used herein, the solution achieved by the neural network is a customized profile of the behavior pattern of the user's heart.

The term learning algorithm denotes a set of well-defined rules for solving a learning problem. There are many different types of learning algorithms specifically for Riven neural network models, and these algorithms differ from each other mostly in the way how weights are modified.

Another important factor is the way in that a neural network relates to the environment. In this context there are the following learning paradigms:

Supervised Learning, when an external agent is used that indicates to the network the desired response for the input pattern;
Non-supervised learning (self-organizing), when there is no external agent indicating the desired response for the input patterns.

It is meant by presentation cycle all N-couples (input and output) from the training set in the learning process. As used in the described method, system and apparatus, the neural network of the DNA Module has the non-supervised learning mode.

The neural network of the DNA Module 19 of the main branch 10 has an Input Layer corresponding to the data collected from the individual 1 and an Output Layer corresponding to a menu containing categories of referential intercurrences.

Returning to FIG. 3, the managing branch 12 comprises the following routine modules that operate under the control of a controller 40:

A Monitoring Module 41—the monitoring module 41 includes the routines for client assistance, clinical research and patient monitoring history;

A Configuration Module 42—the configuration module 42 includes the routines for the classification of intercurrence types and intercurrence groups, routines of actions to be carried out, steps to be performed during assistance and a general symptoms record;

A Network Module 43—the network module 43 includes the routines for user interaction, screens/modes and access profiles;

A Medical Record Module 44—the medical record module 44 includes the routines for recording administered pharmaceuticals and medical specialties;

A Product Module 45—the product module 45 includes the monitoring routines of the MC 2.

A Cooperative and Affiliated Members Register Module 46—this module 46 includes the routines for personnel management and registration; physicians, health entities, healthcare insurance providers and insurance companies and monitors and clients.

In the disclosed examples, the main branch 10 functions within the remote monitoring apparatus of the cardiac condition of an individual. The managing branch 12 is associated with the data interface 6 through which users (physician, patient, and monitoring center personnel) can find the necessary information for monitoring a patient, take a rescue decision, report patient condition, insert a new patient file, exclude former patient file, define a new monitoring network design for specific cases, etc. The interface 6 is the gate through which all interactions between the system parts occur and also a panel providing options and information access. The managing branch 12 is an electronic tool comprising many modules (embodied in software) for operating the system. A non-limiting example of the data interface 6 is shown in FIG. 4.

With reference to FIG. 5, an apparatus 50 for remotely monitoring a cardiac condition of the individual 1 is illustrated. The apparatus 50 is configured to allow the continuous pick-up, analysis and monitoring of the behavior of the user's heart, and to perform an immediate detection, generating an exam to be analyzed by a healthcare professional. In case any intercurrence is detected, the intercurrence is classified in two major groups: arrhythmias and ischaemias, as well as being broken down into their subgroups.

The apparatus 50 has 4 (four) electrodes 52a, 52b, 52c, 52d which allows the picking-up and behavior of the electrical cardiac impulses using the three electrodes 52a-c arranged in the Derivations I, II and III (illustrated in FIG. 6) and the fourth electrode 52d which acts as the ground, reducing noises and interferences with the electrical signals received. From the medical literature, the Derivations I, II, III are the most complete and enable a comprehensive view of the human heart from several angles. The electric signals from the heart are picked up analogically, amplified and converted from the analog format into the digital format. Once in this format, the data is processed on an internal microprocessor which compares them with a database based on neural networks. Upon detecting any difference between the picked up plotting and the recognized database, the apparatus 50 automatically generates an ECG exam, which is transformed into a data packet to be sent via suitable communication techniques, for example via cellular network (GSM/GPRS), to the MC 2 for analysis.

Additionally the apparatus 50 includes a GSM antenna 54 designed as a vertically polarized dipole system; a GPS antenna 56 designed as a horizontally polarized helical system; a hands-free set provided with an omni-directional electret microphone 58; a loudspeaker 60; a plug for connecting the electrode cables to the monitor being of the P2 stereo type with microphone; a set of electrode cables; a tact-switch type button; a side volume control; and circuits with diodes and transistors.

The apparatus 50 also includes a hands-free system such that the MC 2 may contact the individual 1 and vice-versa and the healthcare professionals are able to collect further information from the individual 1 and indicate the best measure for user assistance or, in case the individual is unable to move, dispatching immediately a rescue unit.

The apparatus 50 also has an accelerometer device 62 which is able to identify user falls, a common symptom after a severe heart attack. Therefore an ECG received related to a patient fall requires a still more urgent assistance. A vibrator 64 is provided that, when activated, provides a warning to the individual. Likewise, an alarm 66 is provided that when activated emits an audible alarm, and one or more indicating lights 68 are provide to indicate the operating status of the apparatus 50 but can also emit a visual alarm to the individual. In addition, an SOS/help button 70 is provided which can be pushed by the individual to send a help signal to the MC 2.

Operation of the apparatus 50 is controlled by a suitable controller 72, such as an ARM GSM processing module. The apparatus 50 can be powered by a battery 74.

In order to make easier the localization and guiding of the individual 1 to the nearest Health Center, the apparatus has a GPS-assisted localization system able to provide the location—Latitude and Longitude—to the individual 1 and correlate it with maps and hospital networks to readily assist the individual.

Since it is connected to the cellular network, the apparatus 50 can be handled remotely via software, which allows a remote exam to be generated by a clinician, thus changing the way exams are made in that it no longer depends on the person's will, making data collection possible at any time and at any place having cellular network coverage.

The apparatus 50 has the monitoring function and provides a series of benefits over conventional technologies such as: embodied intelligence, without the need of surgical intervention for installation, improved autonomy, ergonomics and portability.

The apparatus 50 can be portable, mobile, and non-invasive, including hardware, software and a back-office application allowing for the smart and autonomous remote monitoring—via GSM/GPRS, detecting cardiac intercurrences (arrhythmias and ischaemias) through the three electrodes 52a-c, falls, as well as integrating hands-free assistance and geographical localization via GPS and allowing others to track the monitoring via the Internet using the data interface 6.

Therefore, the communications between the individual 1 and the MC 2 may be described as being two-way, since in addition to sending data from the monitored patient to the MC 2, a clinician or the MC may conditionally request, on demand, a new exam at any time.

For consumption management purposes, the system is provided with circuits having diodes and transistors for potentially different situations and battery charge saving.

Cardiac Monitoring

With reference to FIGS. 6 and 7, an exemplary technique of cardiac monitoring will be described. However, other techniques can also be employed.

An ECG comprises recording the electrical phenomena which originate during cardiac activity by means of an apparatus called an electrocardiograph. The electrocardiograph is a galvanometer (an apparatus that measures the potential difference between two points) which measures small current intensities collected from two electrodes (small metal plates connected to a conducting wire) arranged on determined points of the human body. ECG's serve as a valuable aid in the diagnostic of a large number of cardiopathies and other conditions such as, for example, hydroelectrolytic disturbances.

The potential difference between two members was introduced by Einthoven, which conceived the heart in the center of an equilateral triangle whose vertices would be represented by the right arm (R), the left arm (L), and the left leg (F). The positioning of the electrodes and bipolar derivations are made according to Einthoven's triangle (see FIG. 6). This orientation was based on Kirchhoffs second law, which states that in a closed loop, the sum of potential differences equals to zero. In this triangle, Einthoven inverted the polarity of Derivation II in order to obtain a positive record of the wave R in the three derivations.

The connections made are:
Derivation I=VL-VR (left arm—right arm)
Derivation II=VF-VR (left leg—right arm)
Derivation III=VF-VL (left leg—left arm)

The ECG exam is indicated as part of the analysis of heart disease, particularly cardiac arrhythmias and ischaemias. ECG is useful in the diagnostics of acute myocardial infarction, being the preferably adopted exam on emergencies together with the dosage of cardiac enzymes.

This record generated by the ECG exam shows the electric potential variation in time, generating a linear image, on waves. With reference to FIG. 7, these waves follow a rhythmic pattern having a particular terminology.

P wave: corresponds to the atrial depolarization.
QRS complex: corresponds to ventricular depolarization; it is higher than P wave since the muscle mass of the ventricles is greater than that of atria.
T wave: corresponds to ventricular repolarization; the reversal of the T wave indicates an ischemic process.

Upon receiving electric signals from the human body, ranging from 1 mV to 5 mV, these are collected by the three electrodes 52*a-c* arranged as described above. These impulses—having a sampling rate of 360 Hz—are amplified up to 1000 times by means of an operational amplifier. Thereafter, a series of filters are applied to remove interfering noises.

The aim is to remove through successive filtrations the 60 Hz noise from the power grid, the muscle noise (EMG—Electromyogram), and the baseline wander.

In order to remove the noise from the electrical grid, as well as the muscle noise, a Butterworth low-pass band filter having a rejection range (cut frequency) of 40 Hz is used.

For removing the baseline wander, a Butterworth high-pass band filter having a rejection range (cut frequency) of 0.67 Hz is used.

After filtering, indicators (amplitude and time) of the relevant characteristics of the ECG, such as: P wave, QRS complex, T wave, SR segment, RR interval, etc. are extracted and normalized, thus forming a vector to be presented to the input layer of the RNP.

After processing in parallel—verifying a set of previously stored vectors—the RNP decision layer (based upon an algorithm similar to k-nearest neighbor) selects the class (c) that best meets the characteristics shown.

Initially, numerous vector models (based on the database of arrhythmias and ischaemias of MIT-BIH) are stored in the RNP—respectively with the values from the output layer, which form the classes (clusters)—relating to expected results: normal, arrhythmia, ischemia, etc.

Having detected an intercurrence (arrhythmia or ischemia), the 10 seconds during the cardiac event that occurred are stored in a physical file in binary format. These files are kept in a specific directory and can be subsequently retrieved or transferred once again.

Together with data relating to the intercurrence, relevant information is added such as: geographical location of the monitored individual obtained through the longitude and latitude coordinates obtained via GPS (Global Positioning System).

The transmission of these data will be made through the GPRS (General Packet Radio Service) services network which is made available through the GSM (Global System Mobile) connection provided by cell phone signal. For data transmission, the FTP (File Transfer Protocol) is used which allows the transfer from compressed and partitioned files in packets of 256 bytes, from the monitor to a remote data server.

Data compression is performed by using a Linux application known as "gzip". This application compresses using an algorithm based on the public domain Lempel-Ziv code. The data compression is important since:

It permits to reduce the size of data files, enabling the storage of a greater amount of information;
The transfer of smaller files will be carried out much faster; as the data transfer rate is limited in the GSM/GPRS technology, this compression enables a reduction in costs in using the data bandwidth.

Fall detection is another process being executed in parallel. For this purpose, the accelerometer 62 is used, which is able to measure the acceleration of a movement in a three-dimensional axis. By reading these variations it is possible to detect movements—aiding in filtering and removing the artifact motion from the ECG, which interfere with the plotting—as well in identifying falls, whether resulting from an cardiac intercurrence or not. The falls are also monitored and sent to the MC 2, together with the location via GPS and an ECG exam.

The battery consumption is also monitored in a parallel process, wherein upon reaching a critical level the user is warned—via leds and vibration—of the current battery condition, thus suggesting an immediate substitution or recharging of the battery.

The support to the coverage of the GSM cellular network is also monitored, wherein the user is warned—via leds and sound signal—of the current condition. This process involves, upon re-establishing the connection, sending various information, such as: ECG, location, etc. to the MC 2.

At any time the MC 2 or the individual may establish contact via hands-free in order to dispel doubts or request assistance.

An on-demand request can be made from the MC 2 or conditionally by a clinician to request once again an exam allowing confirmation of the received exam which originally raised doubts. This event may be triggered from the back-office application of the MC 2, or by means of a simple SMS from a cell phone.

A specific example of the cardiac monitoring routine is illustrated in FIG. 8. Initially during the routine monitoring 100 of an individual, the monitor detects an irregular heart beating 102. The monitor then generates an ECG 104 and sends it to the MC 2. A clinician in the monitoring center 2 carries out an analysis on the received ECG 106 and the clinician may then decide to request a new ECG 108 or check the symptoms 110 of the patient. The clinician may decide 112 to initiate an assistance action and request the attendant in the monitoring center 2 to initiate an assistance action 114. If the clinician chooses to check the individual's symptoms, he/she may request an attendant to remotely check the symptoms 116. After checking, the attendant sends a new ECG with the symptoms 118 for analysis 120 by the clinician and from this action an assistance action may be initiated.

It is also possible to carry out a remote update of the monitoring module of the apparatus through an Over The Air concept by simply sending a SMS containing specific commands for this case. That is, in case of updating the firmware or software of the monitor itself, the user does not need to be displaced.

The invention may be embodied in other forms without departing from the spirit or novel characteristics thereof. The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. A portable system for remotely monitoring a cardiac condition of an individual, comprising:
 a portable electrocardiogram apparatus that is configured to be physically connected to the individual and to physically accompany the individual, the electrocardiogram apparatus includes a main branch having:
 a main module that is configured to perform activation functions of the electrocardiogram apparatus for monitoring the cardiac condition of the individual;
 an ECG module that is configured to carry out ECG exams evaluated by algorithms provided by a DNA module for checking cardiac intercurrences;
 the DNA module that is configured to detect cardiac intercurrences via a probabilistic neural network;
 a GSM module that is configured to perform a two-way communication between the electrocardiogram apparatus and a monitoring center via GSM/GPRS;
 a GPS module that is configured to read GPS data from the electrocardiogram apparatus and retrieve latitude and longitude coordinates;
 an XYZ module that is configured to read and evaluate coordinates of an accelerometer for fall detection.

2. The system according to claim 1, wherein the probabilistic neural network operates in a non-supervised mode.

3. The system according to claim 1, wherein the probabilistic neural network includes an input layer that comprises ECG data of the individual and an output layer that comprises categories of cardiac intercurrences.

4. The system according to claim 3, wherein a solution achieved by the probabilistic neural network comprises a customized profile of the individual.

5. The system according to claim 1, wherein the main module is configured to perform the following routines:
 initializing the electrocardiogram apparatus and executing the other modules;
 checking an SOS/help button;
 checking a battery level;
 communicating and exchanging information between all the modules;
 requesting the execution of an ECG;
 requesting transfer of a data file to a data server;
 requesting a download of a data file from the data server;
 requesting the sending of a SMS text message;
 requesting the electrocardiogram apparatus to vibrate as a warning;
 requesting a buzzer to emit sound as a warning; and
 requesting an emergency call and/or sending an SMS text message and location warning upon detecting a fall of the individual.

6. The system according to claim 1, wherein the ECG module is configured to answer requests from the main module with respect to execution of ECG's and reading of battery levels.

7. The system according to claim 1, wherein the GSM module is configured to control communications via hands-free phone calling and by sending and receiving SMS text messages.

8. The system according to claim 1, wherein the GSM module is configured to mutually perform the transfer of files and data from the electrocardiogram apparatus to a data server and to forward SMS text message communications that are received to the main module.

9. The system according to claim 1, wherein the GPS module is configured to transmit position coordinates to the main module which in turn is configured to forward the position coordinates to the ECG module.

10. The system according to claim 1, wherein the XYZ module is configured to detect when the electrocardiogram apparatus is moved or falls and is configured to notify the main module.

11. The system according to claim 1, wherein the electrocardiogram apparatus includes a buzzer that is connected to the GSM module.

12. The system of claim 1, further comprising a managing branch associated with a data interface, and the managing branch includes:
 a monitoring module that is configured with routines for individual assistance, clinical research and individual monitoring history;
 a configuration module that is configured to classify intercurrence types and intercurrence groups, and includes routines of actions to be carried out, steps to be performed during assistance, and a general symptoms record;
 a network module that includes routines for user interaction, screens/modes and access profiles;
 a medical record module that includes routines for recording administered pharmaceuticals and medical specialties;
 a product module that includes monitoring routines of a monitoring center;
 a cooperative and affiliated members register module that includes routines for personnel management and registration.

13. The system of claim 1, wherein the electrocardiogram apparatus comprises:
- a plurality of electrodes suitable for connection to the individual;
- a processor;
- a battery providing electrical power to the electrocardiogram apparatus;
- an accelerometer;
- a GSM antenna;
- a GPS antenna; and
- a speaker and a microphone.

14. A portable system for remotely monitoring a cardiac condition of an individual, comprising portable electrocardiogram apparatus that is configured to be physically connected to the individual and to physically accompany the individual, the electrocardiogram apparatus includes a main branch with:
- a controller;
- a main module connected to the controller and that is configured to perform activation functions of the electrocardiogram apparatus for monitoring the cardiac condition of the individual;
- an ECG module connected to the controller and that is configured to generate electrocardiogram exams to be evaluated for checking cardiac intercurrences;
- a DNA module connected to the controller and that is configured to evaluate results of the electrocardiogram exams to detect intercurrences via a probabilistic neural network;
- a communications module connected to the controller and that is configured to perform a two-way communication between the electrocardiogram apparatus and a monitoring center;
- a GPS module connected to the controller and that is configured to read GPS data from the electrocardiogram apparatus and retrieve latitude and longitude coordinates; and
- an XYZ module connected to the controller and that is configured to read and evaluate coordinates of an accelerometer of the electrocardiogram equipment for fall detection.

15. The system of claim 14, wherein the electrocardiogram apparatus includes a buzzer that is connected to the GSM module.

16. The system of claim 14, further comprising a managing branch associated with a data interface, and the managing branch includes:
- a controller;
- a monitoring module connected to the controller;
- a configuration module connected to the controller;
- a network module connected to the controller;
- a medical record module connected to the controller;
- a product module connected to the controller;
- a cooperative and affiliated members register module connected to the controller.

17. The system of claim 14, wherein the electrocardiogram apparatus further comprises:
- a plurality of electrodes suitable for connection to the individual;
- a processor;
- a battery providing electrical power to the electrocardiogram apparatus;
- an accelerometer;
- a GSM antenna;
- a GPS antenna; and
- a speaker and a microphone.

* * * * *